(12) United States Patent
Fong et al.

(10) Patent No.: US 7,387,806 B2
(45) Date of Patent: Jun. 17, 2008

(54) METHOD OF USING GERANIUM OIL AND SOPHORA ROOT EXTRACTS AS A SUPPORTING COMPOSITION IN CANCER TREATMENTS

(75) Inventors: Andy A. T. Fong, Taipei (TW); Guang-Tzuu Shane, Taipei (TW)

(73) Assignee: Medigreen Biotechnology Inc., Panchiao Taipei (TW)

( * ) Notice: Subject to any disclaimer, the term of this patent is extended or adjusted under 35 U.S.C. 154(b) by 457 days.

(21) Appl. No.: 10/984,246

(22) Filed: Nov. 8, 2004

(65) Prior Publication Data

US 2005/0095306 A1   May 5, 2005

Related U.S. Application Data

(63) Continuation of application No. 10/269,165, filed on Oct. 9, 2002, now abandoned.

(60) Provisional application No. 60/327,868, filed on Oct. 9, 2001.

(51) Int. Cl.
*A01N 65/00* (2006.01)
*A61K 36/48* (2006.01)
*A61K 9/48* (2006.01)
*A61K 9/20* (2006.01)
*A61K 47/00* (2006.01)

(52) U.S. Cl. ................ 424/757; 424/439; 424/451; 424/464; 424/725; 424/773; 514/885

(58) Field of Classification Search ................ None
See application file for complete search history.

(56) References Cited

FOREIGN PATENT DOCUMENTS

| CN | 1124604 | 6/1996 |
|---|---|---|
| CN | 1333045 | 6/2001 |
| CN | 1333046 | 6/2001 |
| CN | 1167441 C * | 9/2004 |

OTHER PUBLICATIONS

A Chinese sales brochure entitled "A Brief Introduction of Tzai Szeng (Regenerating) (AT-100)-A New Anti-Cancer Drug" (English translation): publicly available between 1992 and Oct. 8, 2002; 2 pages (Chinese), 3 pages (English translation); published by Cal Herb-Chemistry Lab.

An English product catalogue of Matrine Injection entitled "Catalogue of New Drugs"; publication date unknown; 1 page; published by Shandong Xinhua Pharmaceutical Company Limited.

An English online publication entitled "Sophora" by Subhuti Dharmananda, Ph.D, website http://www.itmonline.org/arts/sohora.htm: Sep. 7, 2001; 12 pages; published online by the Institute for Traditional Medicine.

The chapter entitled "Geranium" (English translation) in the book entitled "Aromatherapy" (cover page showing book title attached); first edition published in Feb. 1996 (page showing publication date attached); 2 pages (Chinese), 2 pages (English translation); published by Shih-Mao Publisher; "Aromatherapy" is a Chinese translation based on the original English book publication entitled "The Directory of Essential Oils" is first published in Great Britain in 1992 by The C.W. Daniel Company Limited.

A Chinese and English product manual of the composition of geranium oil and extractions from roots of Sophora flavescenes entitled "Xiang Shen Capsule Manual"; publicly available in 1992; 1 page (Chinese), 1 page (English).

* cited by examiner

*Primary Examiner*—Michele Flood
(74) *Attorney, Agent, or Firm*—Finnegan, Henderson, Farabow, Garrett & Dunner, L.L.P.

(57) ABSTRACT

A method of administering an herbal composition, comprising geranium oil and extracts from roots of the plants of the genus *Sophora* to mammalian animals undergoing cancer treatments that induce bone marrow suppression side effect, such as chemotherapy and radiation therapy. The composition can be in the form of an oil capsule, tablets, pills, and pastes and administered orally at specific dosages. The composition can also take on the form of an injection to be administered intravenously and intraperitoneally at specific dosages. The administration can be made before and or after the cancer treatment.

59 Claims, 11 Drawing Sheets

Figure 1

GC-MS Result of Geranium Oil Produced in Kuming, China

| Compound | Content (%) |
|---|---|
| Hexanol | 0.05 |
| 3-hexen-1-ol | 0.07 |
| α - pinene | 0.31 |
| β - pinene | 0.11 |
| To be identified | / |
| To be identified | 0.02 |
| To be identified | 0.05 |
| P – cymene | 0.04 |
| Limonene | 0.10 |
| 1,8-cineol | 0.19 |
| Ocimene | 0.04 |
| Linalool oxide | 0.10 |
| Linalool | 3.07 |
| Trans-Rose Oxide | 1.73 |
| Cis-Rose Oxide | 0.62 |
| Citronellal | 0.15 |
| Menthone | 0.75 |
| Iso-menthone | 0.57 |
| Menthol | 0.12 |
| α- terpineol | 0.09 |
| Citronellol | 48.83 |
| Geraniol | 5.72 |
| Citronellyl formate | 11.73 |
| Geranyl formate | 1.30 |
| To be identified | 0.07 |
| To be identified | 0.29 |
| β- caryophellene | 0.54 |
| Citronellyl propionate | 0.98 |
| α- gurjunene | 4.10 |
| To be identified | 0.14 |
| cadiene | 0.96 |
| Others | |

Figure 2

Result of $LD_{50}$ Experiment of Oral Administration of Composition Capsule to Mice

| Dosage (g/kg) | Number of Mice | Number of Deaths | Percentage of Deaths (in decimal points) | $LD_{50}$ and P Value |
|---|---|---|---|---|
| 4 | 10 | 10 | 1.0 | $LD_{50}$=2.35g/kg |
| 3.2 | 10 | 9 | 0.9 | (2.10-2.62g/kg) |
| 2.56 | 10 | 7 | 0.7 | |
| 2.048 | 10 | 3 | 0.3 | P=0.95 |
| 1.638 | 10 | 0 | 0 | |

Figure 3

Result of LD50 Experiment of Intravenous Administration of Composition Injection to
Mice (Injection Over A 90 Seconds Period)

| Dosage mg/kg | Number of Mice | Sex | Route | Symptoms | Number of Deaths |
|---|---|---|---|---|---|
| 240 | 10 | ℵ | iv | When half of the dosage was administered, breathing speeded up and then stopped. | 10 |
| 192 | 10 | ℵ | iv | After the drug was administered, breathing speeded up, absence of activity, absence of righting response, recovered in 5 minutes. | 7 |
| 153.6 | 10 | ℵ | iv | After the drug was administered, remain quiet, absence of activity, decrease in righting response, recovered in 10 minutes | 4 |
| 122.98 | 10 | ℵ | iv | Breathing speeded up a little, absence of activity, recovered in 10 minutes | 1 |
| 98.36 | 10 | ℵ | iv | Same as above | 0 |

By Koarber's Method $LD_{50} = 164.3 \pm 17.6$ mg/kg (P=0.95)

Figure 4

Result of LD50 Experiment of Intraperitoneal Administration of Composition Injection to Mice

| Dosage mg/kg | Number of Mice | Sex | Route | Symptoms | Number of Deaths |
|---|---|---|---|---|---|
| 437.5 | 10 | ♀ | ip | After the drug was administered, mice in sleep state, absence of righting response, died after 24 hours | 10 |
| 350 | 10 | ♀ | ip | After the drug was administered, mice in sleep state, decrease in righting response | 6 |
| 280 | 10 | ♀ | ip | Symptoms as above, but milder, recovered in 3 hours | 1 |
| 224 | 10 | ♀ | ip | Same as above | 0 |

By Koarber's Method $LD_{50} = 334.8 \pm 27.9$ mg/kg (P=0.95)

Figure 5
Dosage Calculation for Oral Administration of Composition Capsule

| | A | B | C | D | E |
|---|---|---|---|---|---|
| 1 | Animal LD50 Experiment Oral Administration | | | | |
| 2 | LD50 Dosate (mg/kg/day) | 2,350.00 | | | |
| 3 | Maximum Tolerated Dosage(mg/kg/day) | 1,638.00 | | | |
| 4 | Minimally Effective Dosage(mg/kg/day) | 150.00 | Based on animal experiment using composition capsule to treat esophageal adenocarcinoma (EAC) | | |
| 5 | | | | | |
| 6 | Conversion to Human Dosages | | | | |
| 8 | Maximum Tolerated Dosage(mg/60kg/day) | 9,828.00 | = (1638/10) x 60 | | |
| 9 | Minimally Effective Dosage(mg/60kg/day) | 900.00 | =(150/10) x 60 | | |
| 10 | | | | | |
| 11 | Composition Capsule (Botanical Drug Product) | | | | |
| 12 | Human Maximum Tolerated Dosage (capsule/60kg/day) | 24.57 | = 9828/400 | | |
| 13 | Human Regular Dosage(capsule/60kg/day) | 9.00 | | | |
| 14 | Human Minimally Effective Dosage(capsule/60kg/day) | 2.25 | = 900/400 | | |
| 15 | Main Ingredients Per Capsule (mg) | 400.00 | | | |
| 16 | From Geranium Oil | 390.00-398.00 | | | |
| 17 | From Sophora roots extracts | 2.00 - 10.00 | | | |
| 18 | | | | | |
| 19 | Herbal Extracts (Botanical Drug Substance) | Geranium Oil | | Sophora roots extracts | |
| 20 | Human Maximum Tolerated Dosage (mg/60kg/day) | 9,582.30 - 9778.86 | = 24.57 x 400 x (390/400) = 24.57 x 400 x (398/400) | 49.14 - 245.70 | = 24.57 x 400 x (2/400) = 24.57 x 400 x (10/400) |
| 21 | Human Regular Dosage(mg/60kg/day) | 3,510.00 - 3,582.00 | = 9 x 400 x (390/400) = 9 x 400 x (398/400) | 18.00 - 90.00 | = 9 x 400 x (2/400) = 9 x 400 x (10/400) |
| 22 | Human Minimally Effective Dosage(mg/60kg/day) | 877.50 - 895.50 | = 2.25 x 400 x (390/400) = 2.25 x 400 x (398/400) | 4.50 - 22.50 | = 2.25 x 400 x (2/400) = 2.25 x 400 x (10/400) |
| 23 | | | | | |
| 24 | Botanical Raw Material | Pelargonium graveolens (stem and leaves) | | Sophora roots | |
| 26 | Human Maximum Tolerated Dosage (mg/60kg/day) | 9,582,300 - 9,778,860 | = 9582.30/0.001 = 9778.86/0.001 | 1,638 - 8,190 | = 49.14/0.03 = 245.70/0.03 |
| 27 | Human Regular Dosage(mg/60kg/day) | 3,510,000 - 3,582,000 | = 3510.00/0.001 = 3582.00/0.001 | 600 - 3,000 | = 18/0.03 = 90.00/0.03 |
| 28 | Human Minimally Effective Dosage(mg/60kg/day) | 877,500 - 895,500 | = 877.50/0.001 = 895.50/0.001 | 150 - 750 | = 4.5/0.03 = 22.50/0.03 |
| 29 | Proportion of geranium oil to raw material | 0.001 | | | |
| 30 | Proportion of Sophora roots extracts to raw material | 0.030 | | | |

Figure 6
Dosage Calculation for Intravenous Administration of Composition Injection

| | A | B | C | D | E |
|---|---|---|---|---|---|
| 1 | Animal LD50 Experiment IV Administration | | | | |
| 2 | LD50 Dosage (mg/kg - day) | 164.00 | | | |
| 3 | Maximum Tolerated Dosage(mg/kg/day) | 98.00 | | | |
| 4 | Minimally Effective Dosage(mg/kg/day) | 25.00 | Based on animal experiment using composition vaccine to treat esophageal adenocarcinoma (EAC) | | |
| 5 | | | | | |
| 6 | Conversion to Human Dosages | | | | |
| 7 | LD50 Dosage(mg/60kg/day) | 984.00 | = (164/10) x 60 | | |
| 8 | Maximum Tolerated Dosage(mg/60kg/day) | 588.00 | = (98/10) x 60 | | |
| 9 | Minimally Effective Dosage(mg/60kg/day) | 150.00 | = (25/10) x 60 | | |
| 10 | | | | | |
| 11 | Composition Injection (Botanical Drug Product) | | | | |
| 12 | Human Maximum Tolerated Dosage (ampoule/60kg/day) | 2.94 | = 588/200 | | |
| 13 | Human Regular Dosage (ampoule/60kg/day) | 1.00 | | | |
| 14 | Human Minimally Effective Dosage (ampoule/60kg/day) | 0.75 | = 150/200 | | |
| 15 | Active ingredients per vaccine (mg) | 200.00 | | | |
| 16 | From geranium oil | 198.76 - 198.30 | | | |
| 17 | From Sophora roots extractions | 1.24 - 1.70 | | | |
| 18 | | | | | |
| 19 | Herbal Extracts (Botanical Drug Substance) | Geranium Oil | | Sophora Roots | Extracts |
| 20 | Human Maximum Tolerated Dosage (mg/60kg/day) | 583.00 - 584.35 | = 2.94 x 200 x (198.30/200) = 2.94 x 200 x (198.76/200) | 3.65 - 5.00 | = 2.94 x 200 x (1.24/200) = 2.94 x 200 x (1.70/200) |
| 21 | Human Regular Dosage (mg/60kg/day) | 198.30 - 198.76 | = 1 x 200 x (198.30/200) = 1 x 200 x (198.76/200) | 1.24 - 1.70 | = 1 x 200 x (1.24/200) = 1 x 200 x (1.70/200) |
| 22 | Human Minimally Effective Dosage (mg/60kg/day) | 148.73 - 149.07 | = 0.75 x 200 x (198.30/200) = 0.75 x 200 x (198.76/200) | 0.93 - 1.28 | = 0.75 x 200 x (1.24/200) = 0.70 x 200 x (1.70/200) |

Figure 7
Dosage Calculation for Intraperitoneal Administration of Composition Injection

| | A | B | C | D | E |
|---|---|---|---|---|---|
| 1 | Animal LD50 Experiment IV Administration | | | | |
| 2 | LD50 Dosage (mg/kg - day) | 335.00 | | | |
| 3 | Maximum Tolerated Dosage(mg/kg/day) | 224.00 | | | |
| 4 | Minimally Effective Dosage(mg/kg/day) | 25.00 | Based on experiment from use of vaccine in esophageal adenocarcinoma (EAC) | | |
| 5 | Conversion to Human Dosages | | | | |
| | LD50 Dosage (mg/60kg/day) | 2,010.00 | = (335/10 x 60) | | |
| | Maximum Tolerated Dosage (mg/60kg/day) | 1,344.00 | = (224/10 x 60) | | |
| | Minimally Effective Dosage (mg/60kg/day) | 150.00 | = (25/10 x 60) | | |
| 6 | Composition Injection (Botanical Drug Product) | | | | |
| 7 | Human Maximum Tolerated Dosage (ampoule/60kg/d | 6.72 | = 1344/200 | | |
| 8 | Human Regular Dosage (ampoule/60kg/day) | 1.00 | | | |
| 9 | Human Minimally Effective Dosage (ampoule/60kg/d | 0.75 | = 150/200 | | |
| 10 | Active ingredients per vaccine (mg) | 200.00 | | | |
| 11 | From geranium oil | 198.30 - 198.76 | | | |
| 12 | From Sophora roots extractions | 1.24 - 1.70 | | | |
| 13 | | | | | |
| 14 | Herbal Extracts (Botanical Drug Substance) | Geranium Oil | | Sophora Roots | Extracts |
| 15 | Human Maximum Tolerated Dosage (mg/60kg/day) | 1332.58 - 1335.67 | = 6.72 x 200 x (198.30/200) = 6.72 x 200 x (198.76/200) | 8.33 - 11.42 | = 6.72 x 200 x (1.24/200) = 6.72 x 200 x (1.70/200) |
| 16 | Human Regular Dosage (mg/60kg/day) | 198.30 - 198.76 | = 1 x 200 x (198.30/200) = 1 x 200 x (198.76/200) | 1.24 - 1.70 | = 1 x 200 x (1.24/200) = 1 x 200 x (1.70/200) |
| 17 | Human Minimally Effective Dosage (mg/60kg/day) | 148.73 - 149.07 | = 0.75 x 200 x (198.30/200) = 0.75 x 200 x (198.76/200) | 0.93 - 1.28 | = 0.75 x 200 x (1.24/200) = 0.75 x 200 x (1.70/200) |

Figure 8

Result of Intraperitoneal Administration of Composition Injection to Mice Treated with
5-Fu – Differential Blood Cell Counts

| Treatment | Route | Dose | N | Cell Counts (X ± SEM) and % of Vehicle Control | | |
|---|---|---|---|---|---|---|
| | | | | RBC ($10^6/\mu l$) | PLT ($10^3/\mu l$) | WBC ($10^3/\mu l$) |
| Vehicle | IP | 10 mL/kg x 7 | 1 | 10.40 | 991 | 2.6 |
| (0.025%Tween80 | | | 2 | 9.14 | 628 | 4.7 |
| In 5%Dextrose) | | | 3 | 9.46 | 952 | 2.0 |
| +5FU | | | 4 | 10.50 | 964 | 2.3 |
| | | | 5 | 10.10 | 1053 | 2.6 |
| | | | 6 | 8.35 | 624 | 1.9 |
| | | | 7 | 10.00 | 1074 | 2.5 |
| | | | 8 | 9.65 | 1475 | 4.3 |
| | | | X | 9.70 | 970.1 | 2.86 |
| | | | SEM | 0.25 | 95.5 | 0.37 |
| | | | % | (100) | (100) | (100) |
| PT#1014519-ADD | IP | 100 mg/kg x 7 | 1 | 11.70 | 1310 | 3.3 |
| (ATF-1)(AT-21) | | | 2 | 9.24 | 730 | 3.0 |
| +5FU | | | 3 | 6.25 | 1330 | 5.6 |
| | | | 4 | 9.85 | 807 | 3.5 |
| | | | 5 | 12.10 | 1451 | 3.4 |
| | | | 6 | 9.65 | 815 | 3.7 |
| | | | 7 | Died | Died | Died |
| | | | 8 | Died | Died | Died |
| | | | X | 9.80 | 1073.8 | 3.75 |
| | | | SEM | 0.85 | 131.7 | 0.38 |
| | | | % | (101) | (111) | (131) |
| | IP | 50 mg/kg x 7 | 1 | 9.51 | 762 | 4.9 |
| | | | 2 | 10.30 | 943 | 4.7 |
| | | | 3 | 8.48 | 662 | 4.8 |
| | | | 4 | 8.00 | 1190 | 4.2 |
| | | | 5 | 9.96 | 1268 | 4.8 |
| | | | 6 | 8.28 | 1188 | 4.0 |
| | | | 7 | 8.48 | 1140 | 3.6 |
| | | | 8 | 8.82 | 1096 | 5.8 |
| | | | X | 8.98 | 1031.1 | **4.60 |
| | | | SEM | 0.30 | 77.7 | 0.24 |
| | | | % | (93) | (106) | (161) |

ATF-1 (100 and 50 mg/kg) and vehicle control were administered intraperitoneally (IP) to test animals at 24 hours before and after 5-Fluorouracil (100 mg/kg, PO) for 6 consecutive days. Animals were bled retroorbitally on day 8 for determination of erythrocytes (RBC), platelets (PLT), total leukocytes (WBC). The mean ± SEM was calculated and unpaired Student's $t$ test was applied for comparison between vehicle and compound-treated groups. Differences were considered significant $P<0.05$ (*), $P<0.01$(**)

Note: At 100 mg/kg, IP of ATF-1, 6 of 8 testing animals exhibited diarrhea and muscle relaxation symptoms on day 5, 6 and 7 and 2 out of 8 test animals died on day 7.

Figure 9

Result of Intraperitoneal Administration of Composition Injection to Mice Treated with 5-Fu – Differential Leukocyte Cell Counts

| Treatment | Route | Dose | N | Cell Counts (X ± SEM) and % of Vehicle Control | | |
|---|---|---|---|---|---|---|
| | | | | GR ($10^3/\mu l$) | LY ($10^3/\mu l$) | MO ($10^3/\mu l$) |
| Vehicle (0.025%Tween80 In 5%Dextrose) +5FU | IP | 10 ml/kg x 7 | 1 | 0.5 | 1.7 | 0.4 |
| | | | 2 | 1.2 | 3.0 | 0.5 |
| | | | 3 | 0.5 | 1.1 | 0.4 |
| | | | 4 | 0.6 | 1.5 | 0.2 |
| | | | 5 | 0.5 | 1.6 | 0.5 |
| | | | 6 | 0.2 | 1.6 | 0.1 |
| | | | 7 | 0.5 | 1.6 | 0.4 |
| | | | 8 | 0.7 | 2.5 | 1.1 |
| | | | X | 0.59 | 1.83 | 0.45 |
| | | | SEM | 0.10 | 0.22 | 0.11 |
| | | | % | (100) | (100) | (100) |
| PT#1014519-ADD (ATF-1)(AT-21) +5FU | IP | 100 mg/kg x 7 | 1 | 1.3 | 1.2 | 0.8 |
| | | | 2 | 1.0 | 1.2 | 0.8 |
| | | | 3 | 2.5 | 2.5 | 0.6 |
| | | | 4 | 1.0 | 2.2 | 0.3 |
| | | | 5 | 1.5 | 1.2 | 0.7 |
| | | | 6 | 0.7 | 2.3 | 0.7 |
| | | | 7 | Died | Died | Died |
| | | | 8 | Died | Died | Died |
| | | | X | *1.33 | 1.77 | 0.65 |
| | | | SEM | 0.26 | 0.26 | 0.08 |
| | | | % | (225) | (97) | (144) |
| | IP | 50 mg/kg x 7 | 1 | 1.1 | 3.2 | 0.6 |
| | | | 2 | 1.0 | 3.1 | 0.6 |
| | | | 3 | 1.3 | 3.2 | 0.3 |
| | | | 4 | 1.2 | 2.6 | 0.4 |
| | | | 5 | 1.4 | 3.0 | 0.4 |
| | | | 6 | 1.0 | 2.4 | 0.6 |
| | | | 7 | 1.0 | 2.2 | 0.4 |
| | | | 8 | 1.2 | 3.6 | 1.0 |
| | | | X | **1.15 | **2.91 | 0.54 |
| | | | SEM | 0.05 | 0.17 | 0.08 |
| | | | % | (195) | (159) | (120) |

ATF-1 (100 and 50 mg/kg) and vehicle control were administered intraperitoneally (IP) to test animals at 24 hours before and after 5-Fluorouracil (100 mg/kg, PO) for 6 consecutive days. Animals were bled retroorbitally on day 8 for determination of erythrocytes (RBC), platelets (PLT), total leukocytes (WBC). The mean ± SEM was calculated and unpaired Student's $t$ test was applied for comparison between vehicle and compound-treated groups. Differences were considered significant $P<0.05$ (*), $P<0.01$ (**)

Note: At 100 mg/kg, IP of ATF-1, 6 of 8 testing animals exhibited diarrhea and muscle relaxation symptoms on day 5, 6 and 7 and 2 out of 8 test animals died on day 7.

Figure 10

Pharmcokinetics curve showing different absorption and metabolism rate of intravenously injected matrine and matrine with geranium oil

Figure 11

Pharmcokinetics curve showing different absorption and metabolism rate of intravenously injected Oxymatrine and Oxymatrine with geranium oil % METHOD OF USING GERANIUM OIL AND SOPHORA ROOT EXTRACTS AS A SUPPORTING COMPOSITION IN CANCER TREATMENTS This is a continuation of application Ser. No. 10/269,165, filed Oct. 9, 2002 now abandoned, and claims the benefit of U.S. provisional application No. 60/327,868, filed Oct. 9, 2001, all of which are incorporated herein by reference.

BACKGROUND OF THE INVENTION

1. Field of Invention

This invention relates generally to the use of a supporting composition in cancer treatments and more particularly to administering an herbal composition together with chemotherapy or radiation therapy (or both) in the treatment of cancer.

2. Description of Related Art

Normal cells grow and divide in an orderly and controlled manner. Cancer is a disease where cells become abnormal (cancerous cells) and begin to multiply without control to develop into an extra mass of tissue called a tumor. These cancerous cells can invade nearby tissues and spread through the blood stream and lymphatic system to other parts of the body.

Currently, the four primary types of cancer treatments are immunotherapy, surgery, radiation therapy, and chemotherapy. These cancer treatments may be applied alone or in conjunction with one another. Thus a cancer patient may undergo one or more treatments at a time. A single treatment would span a period of time with therapies delivered at various timed intervals. Immunotherapy, also known as biological therapy or biological response modifier (BRM) therapy, tries to stimulate or restore the ability of the immune system to fight the disease. It is also used to lessen immune system related side effects that may be caused by some cancer treatments. Surgery seeks to directly remove the tumor from the body.

Radiation therapy, also known as radiotherapy, uses high-energy radiation from x-rays, gamma rays, neutrons, and other sources to kill cancer cells and shrink tumors by damaging the cells' genetic material. While cancerous cells are damaged permanently and eventually die, normal cells that are damaged in radiation therapy are able to repair themselves. Side effects that can occur during radiation therapy are skin irritation and hair loss in the area being treated and damage to the bone marrow.

Chemotherapy uses cytotoxic drugs, alone or in combination, to destroy cancer cells. Just as in radiation therapy, cancer cells can be damaged and eventually die. But healthy cells affected in the process can repair themselves after the chemotherapy. Cytotoxic drugs work by interfering with the ability of a growing cell to divide and reproduce itself. Thus, in addition to cancerous cells, other normal fast-dividing growing cells can also be affected. There can be an effect on blood cells forming in the bone marrow causing bone marrow suppression. There can also be an effect on cells in the digestive tract, in the lining of the mouth and in the reproductive system causing diarrhea and mouth soreness, and an effect on hair follicles causing hair loss.

Bone marrow suppression is one of the many side effects of chemotherapy and radiation therapy. It results in reduced blood cell production, including red blood cells, white blood cells, and platelets. Consequently, the patient will experience tiredness, from anemia, become more susceptible to infections, from leukopenia, and bruise easily and bleed more when getting a cut, from thrombocytopenia.

Drugs are used to counter the bone marrow suppression side effect. Epogen (*Epoietin alpha*) has been used to counter the side effect of anemia in cancer chemotherapy, and WinRho SD has been used to counter the side effect of thrombocytopenia.

Many of the treatments developed to coordinate with chemotherapy and radiation therapy to counter the side effect of leukopenia act on specific types of white blood cells, i.e. granulocytes, monocytes, and lymphocytes. Neupogen is a recombinant human granulocyte colony-stimulating factor that stimulates the growth of neutrophils. Leukine is a recombinant human granulocyte-macrophage colony-stimulating factor that stimulates the production of neutrophils and macrophages. In animal laboratories and clinical trials, various interleukins, secreted by T-lymphocytes, have been used to stimulate productions of various white blood cells in the course of chemotherapy. Interleukin 1 (IL-1) is responsible for B-cell and T-cell proliferation, Interleukin 2 (IL-2) is responsible for the proliferation, growth, and activation of B-cells and T-cells, Interleukin 15 (IL-15) appears to be required for natural killer cells (NK cells) and CD8+ Tcells.

Herbs have also been found to counter leukopenia side effect. For example, injection of extracts from *Sophora flavescenes* roots has been reported to have reduced leukopenia side effects of chemotherapy and radiation therapy. Also, injection of *Unicaria tomentosa* water extracts in rats experiencing leukopenia from chemotherapy led to an increase in white blood cells.

BRIEF SUMMARY OF THE INVENTION

The present invention is directed to a method of using an herbal composition in cancer treatments, preferably to reduce the bone marrow suppression side effect of such treatments. The herbal composition is made of geranium oil and extracts from root of plants of the genus *Sophora* (*Sophora* plants), preferably *Sophora falvescenes*. The above "geranium oil" and "extracts from the root of *Sophora* plants" preferably refers to the main ingredients directly extracted from the oil and the root respectively but also includes main ingredients that are chemically synthesized or otherwise provided. The herbal composition can be administered via various routes, i.e. oral, intravenous, or intraperitoneal, in specific dosages to mammalian animals undergoing chemotherapy or radiation therapy.

The method generally involves locating one or more mammalian animals being treated with one or more cancer treatments, but may also involve identifying one or more mammalian animals in need of cancer treatment and administering the above-mentioned composition and one or more cancer treatments. Also, the method generally involves preparing a therapeutically effective dosage of the composition, but may also simply involve use of a previously prepared dosage of the composition.

BRIEF DESCRIPTION OF DRAWINGS

FIG. 5 illustrates the dosage calculation for oral administration of the composition to humans. Based on the $LD_{50}$ experiment with mice as described above in FIG. 2, the maximum tolerated dosage for humans is derived. The minimally effective dosage of the composition for humans is derived basing on animal experiment of using the composition to treat EAC. Dosage in term of a composition of the present invention in capsule form is derived based on weight of the main ingredients per capsule. Dosage in term of the two herbal extracts is derived based on the relative proportion of the two extracts in the capsule. Dosage in term of the raw material is derived based on proportion of each herbal extract to each raw material respectively.

FIG. 6 illustrates the dosage calculation for intravenous administration of the composition to humans. Based on the $LD_{50}$ experiment with mice as described above in FIG. 3, the maximum tolerated dosage for humans is derived. The minimally effective dosage of the composition is derived basing on animal experiment of using the composition to treat EAC. Dosage in term of a composition of the present invention in injection form is derived based on weight of the main ingredients per injection. Dosage in term of the two herbal extracts is derived based on the relative proportion of the two extracts in the injection.

FIG. 7 illustrates the dosage calculation for intraperitoneal administration of the composition to animals. The maximum tolerated dosage, for animals, is based on the $LD_{50}$ experiment with mice as described above in FIG. 4. The minimally effective dosage of the composition is derived basing on animal experiment of using the composition to treat EAC. Dosage in term of a composition of the present invention in injection form is derived based on weight of the main ingredients per injection. Dosage in term of the two herbal extracts is derived based on the relative proportion of the two extracts in the injection.

FIG. 8 shows the differential blood cell counts of erythrocytes (RBC), platelets (PLT), and total leukocytes (WBC) in mice treated with 5-Fu and a composition of the present invention in injection form. The erythrocytes, platelets, and leukocyte counts in mice treated with 5-Fu and the composition of the present invention have increased across the board as compared to the mice treated with 5-Fu only. The total leukocyte count in mice treated with 5-Fu and the composition of the present invention is significantly greater than the leukocyte count in mice treated with 5-Fu only. The result also shows the is 50 mg/kg dosage is better than the 100 mg/kg dosage.

FIG. 9 shows the differential leukocyte counts of granulocytes (GR), monocytes (MO), and lymphocytes (LY) in mice treated with 5-Fu and a composition of the present invention in injection form. The granulocytes, monocytes, and lymphocytes counts of mice treated with 5-Fu and the composition of the present invention is greater than the respective leukocyte counts in mice treated with 5-Fu only. The result is particularly significant with respect to granulocytes and lymphocytes.

DETAILED DESCRIPTION OF THE INVENTION

The present invention relates to methods of using an herbal composition made from geranium oil and extracts from the root of *Sophora* plants, preferably *Sophora flavescenes* (*Sophora* roots) as a supporting drug or supplement in cancer treatments, preferably to reduce the bone marrow suppression side effect occurring in most of such treatments. As a single treatment would span a period of time with therapies delivered at various timed intervals, i.e. a treatment course, the term cancer treatments in its plural form refers to courses of treatments.

1. Geranium Oil

Figure 1:
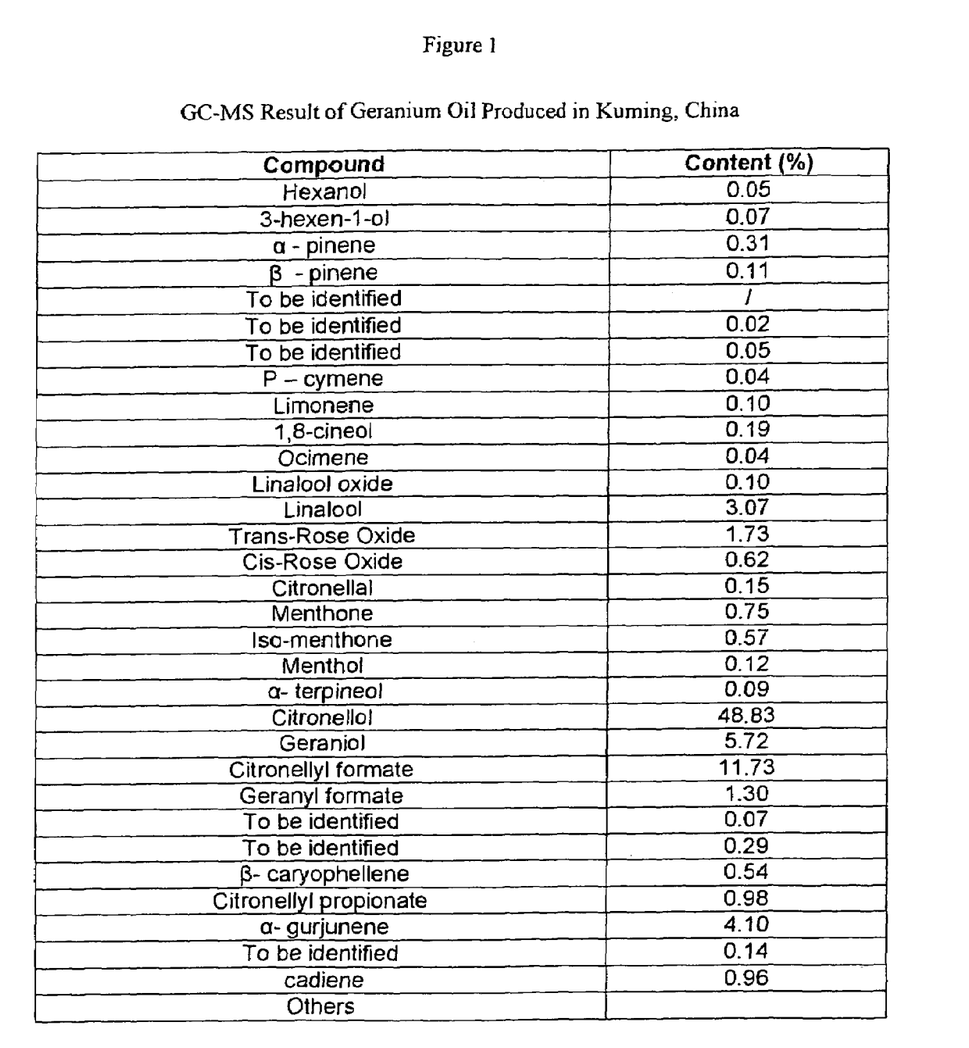
FIG. 1 shows the compounds identified and their relative contents in the geranium oil produced in Kunming, China by the methods of gas chromatography/mass spectroscopy.

Geranium oil may be collected from steam distillation of the stem and leaves of the plant of division Magnoliophyta, class Magnoliopsida, order Geraniales, family Geraniaceae, and genus *Pelargonium*. *Pelargoniums* are native to South Africa and there are more than one hundred species in existence today, including hybridized garden species. *Pelargoniums* are now grown, and geranium oil is now produced, mainly in Algeria, Egypt, Morocco, Bourbon, China, and Australia. The present invention preferably uses geranium oil extracted from *Pelargonium graveolens* or *Pelargonium roseum* and *Pelargonium terebinthinceum* grown in Kunming City of the Yunan Province in China. A gas chromatography/mass spectroscopy (GC-MS) result of the geranium oil produced in Kunming shows the constituent compounds and their relative contents, see FIG. 1. The generally known main constituents of geranium oil are citronellol, geraniol, geranyl fonnate, and citronellyl formate.

Certain specifications of geranium oil are set out in the National Standard of the People's Republic of China—GB 11959-89 which is incorporated herein by reference in their entirety, including any drawings. It adopts the same international standard of ISO 4731:1978 Oil of Geranium (Geranium Oil Standard). The Geranium Oil Standard specifies the outward characteristics of geranium oil, i.e. the geranium oil takes on a clear oil liquid form of a yellow greenish or amber color and has a distinct aroma. The same standard also specifies a relative density of 0.881-0.900 $g/cm^3$, an optical rotation of −6° to −14°, and a refractive index of 1.459-1.466 for geranium oil. In addition, a method, using acetylation and saponification, is prescribed by the same Geranium Oil Standard to determine the total alcohol content of geranium oil.

In order to ensure the quality of the geranium oil used in the present invention, the geranium oil used preferably is first examined for compliance with the specifications of the Geranium Oil Standard. The outward characteristics of the geranium oil are checked in terms of color and aroma. The relative density, optical rotation, and refractive index of the geranium oil used are determined by tests prescribed by the Pharmacopoeia of the People's Republic of China, Appendix VII A, E, and F respectively (incorporated herein by reference in its entirety, including any drawings). The test results showed that the geranium oil has a relative density at 20° C. of 0.889 to 0.899 g/cm³, an optical rotation of −9° to −10° and a refractive index of 1.4595 to 1.4612. These are all within the ranges prescribed by the Geranium Oil Standard as stated above. The total alcohol content, determined in accordance with the method prescribed by the Geranium Oil Standard, is about 71.48% to 72.76% which is well above the 65% alcohol content requirement (65% alcohol content is calculated as geraniol) specified by the Geranium Oil Standard.

2. Sophora Root

Figure 10:
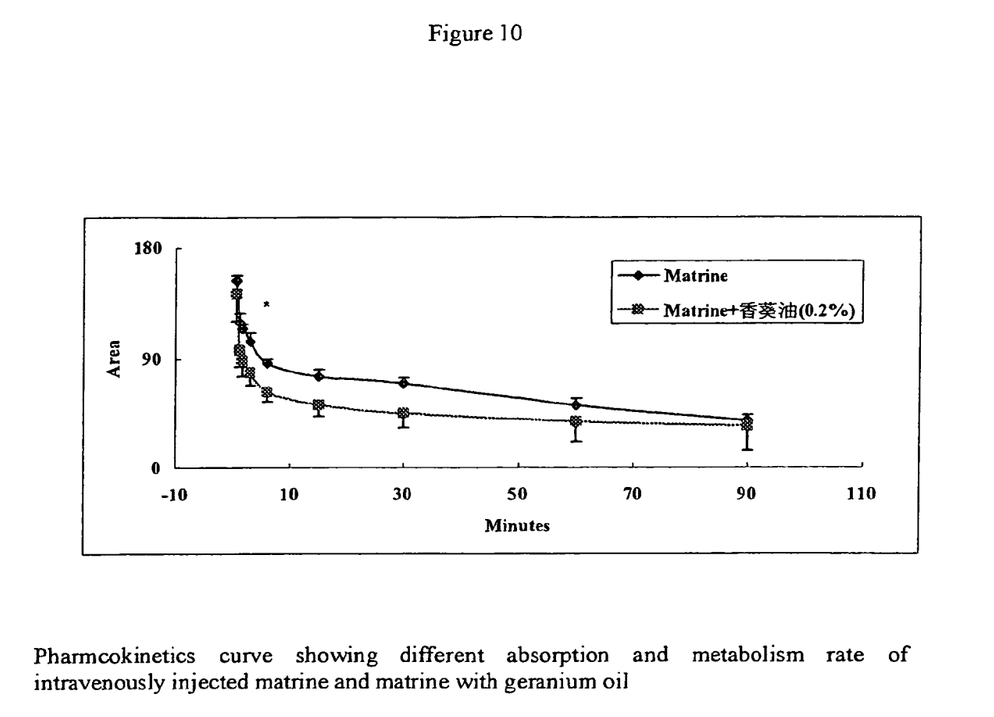
FIG. 10 shows the result of pharmcokinetics study of intravenous injection of matrine and matrine with and addition of geranium oil.
Figure 11:
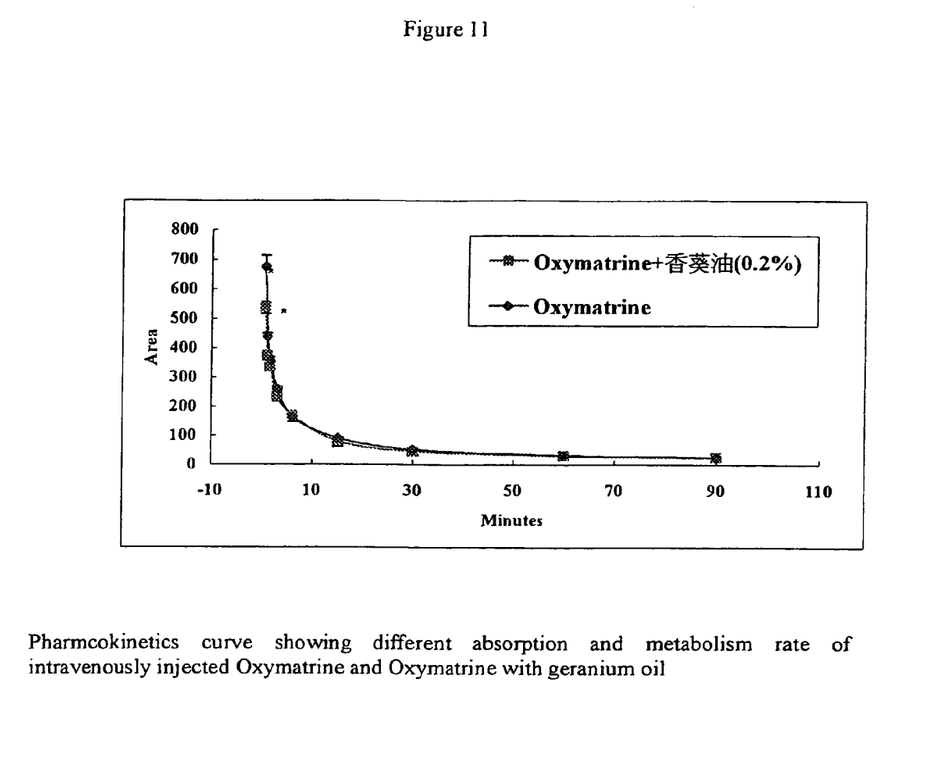
FIG. 11 shows the result of pharmcokinetics study of intravenous injection of oxymatrine and oxymatrine with the addition of geranium oil.

The Sophora root typically is about 10-30 cm long, 1-2 cm in diameter and generally takes on a grayish brown or grayish yellow color. The root preferably has a mild scent and an extremely bitter taste. It is grown mainly in China, Korea, and Japan. Presently, the alkaloids identified in Sophora roots are matrine, oxymatrine, sophoranol, N-methylcytisine, anagyrine, baptifoline, sophocarpine, sophoridine, iso matrine, 7,11-Dehydromatrine, sophoramine, 7-Dehydrosophoramine, 9α-Hydroxy-Sophoramine, 5α,9α-Dihydroxymatrine, N-Oxysophocarpine, sophoranol N-oxide, rhombifoline, Lupanine, Mamanine, Kuraramine, Isokuraramine, Kurarinol. The known main constituents are matrine, oxymatrine. The principal main constituents of Sophora flavescenes are also found in Sophora subprostrata, Sophora tonkinensis, Sophora alopecuroides, Sophora moorcroftiana, and Euchresta strigillosa. Result of pharmcokinetics study shows that in intravenous injections, the addition of geranium oil to matrine or oxymatrine will increase the absorption and metabolism of the respective compound (please see FIG. 10 and FIG. 11).

To ensure the quality of the Sophora roots used, the Sophora roots preferably are first checked for their outer appearance. Thin layer chromatography testing is preferably also applied in accordance with the Sophora root identification method as promulgated in the Pharmacopoeia of the People's Republic of China, Appendix VI B (incorporated herein by reference in its entirety, including any drawings) to determine presence of matrine, oxymatrine and sophocarpine. A titration method as prescribed by the Pharmacopoeia of the People's Republic of China for the determination of the total alkaloid content of Sophora roots may be applied. The total alkaloid content preferably should not be less than 2%. Sophora roots used in the present invention preferably have a total alkaloid content of about 2.74% to 3.03%.

3. Capsules

After examining the geranium oil and the Sophora roots for compliance with the specifications as described above, the composition can be made into an oil capsule through the following preferred steps. 1,000 capsules can be made from the amount of the ingredients described below. 300 to 400 grams of Sophora roots is mixed thoroughly with ethanol in an amount of 1/10 of the weight of the Sophora roots, and then the mixture is smothered for about 12-15 hours. Then the Sophora roots are dried on low heat. The dried Sophora roots are then ground into powder and filtered through 40 mesh. The filtered through Sophora roots powder is then added to 70%-80% ethanol, in an amount of 10 times the weight of the filtered Sophora roots powder, in a steam distillation bottle to heat and reflux the mixture for 2 to 4 hours. The solution is filtered out and placed aside. Ethanol, in an amount of 6 times the weight of the filtered Sophora roots powder, is added to the steam distillation bottle with the Sophora roots powder to heat and reflux for the second time for another 2-4 hours. The solution is filtered out and placed aside. The two filtered liquids are combined and added to the ethanol collector to condense and collect ethanol and to obtain the Sophora paste (which is of a brownish yellow color and tastes extremely bitter).

The Sophora paste preferably should be tested for its total alkaloid content using the Sophora roots extraction content determination method specified in the Pharmaceutical Product Standard of Heilongiang Province (incorporated herein by reference in its entirety, including any drawings). The total alkaloid content is about 70% to 73% (calculated as oxymatrine). The paste then is dissolved with distilled water, and then 5 to 7 grams of glycerine and 250 to 270 grams of gelatin are added (mixture). After the mixture of Sophora paste, glycerine, and gelatin is completely dissolved, it is placed in the vacuum melting bottle to eliminate the air bobble and the water content until the viscosity reaches about 30-50 pa.s. The mixture of Sophora paste, glycerine, and gelatin and 350 to 450 grams of geranium oil are separately inserted into a capsule making machine. Wherein the mixture of Sophora paste, glycerine, and gelatin forms the capsule shell with geranium oil filling the inside of the composition capsule. The capsules are then parched at 35° C. to 45° C. for 10-15 hours. The total alkaloid content of the entire capsule is 2% to 10% total alkaloid/capsule through an analysis of the capsule shell by the spectrophotometric method of the Pharmacopoeia of the People's Republic of China, Appendix VA.

The Sophora paste may be mixed with glycerol soylecithin and then mixed with geranium oil to produce a form of emulsion for oral intake. Cyclodextrin may also be used to make tablets or pills enclosing the composition. The composition can also be made into dietary supplement, health food (functional food), and food additives. One can also decoct the Pelargonium plant and Sophora roots to obtain a liquid form of the composition for direct oral intake as a medicine soup or for making into syrup or other forms of liquid composition. Sophora roots the Pelargonium plant can also be taken orally, in an edible form, separately at a timed interval.

4. Injections

The composition can also be prepared for injections through the following preferred steps. Sophora roots and geranium oil should be examined for compliance with the specifications as stated above. The Sophora roots are ground into coarse powder. 300 grams of the Sophora roots powder is added to 1200 milliliters of geranium oil in a 2000 ml glass heating tube to heat and reflux at 115° C. for 6 hours, and then the liquid is filtered to obtain 800 milliliters of dark yellow clear liquid oil. The oil liquid is placed in a pestle bowl and Tween-80 in 5% Dextrose is slowly added to the bowl while grinding at the same time until the oil liquid becomes transparent and its pH is 6.8 to 7.0. The solution is then filtered, and the filtered solution is placed in a 2 ml ampoule. The ampoule is then sealed and sterilized at 110° C.

5. Dosages

The composition can be administered orally, intraperitoneally, and intravenously at various dosages. Results from $LD_{50}$ (50% lethality) experiments with mice administered orally, intraperitoneally, and intravenously with the composition provide guidance on the range of safe dosages, i.e. maximum tolerated dosage.

LD$_{50}$ Animal Experiment With Oral Administration

Figure 2:
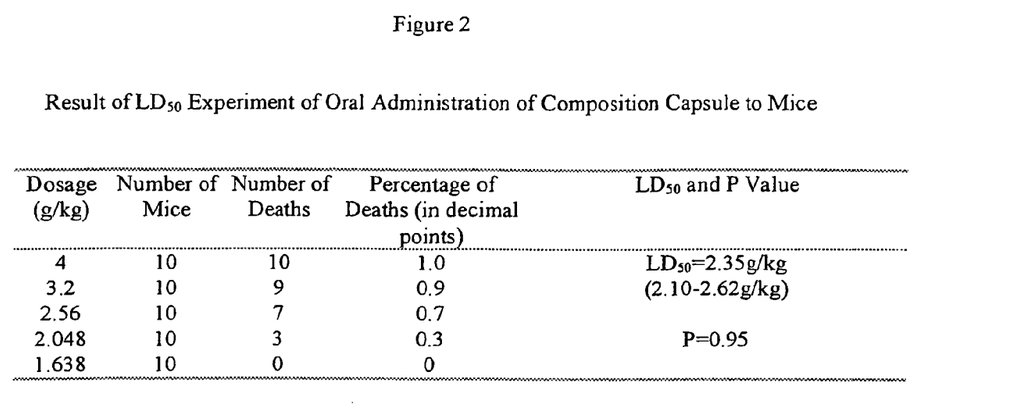
FIG. 2 shows the result of a $LD_{50}$ experiment involving oral administration of a composition of the present invention in capsule form to mice. According to the result, half of the tested mice will die at the dosage of 2.35 g/kg of composition capsule, and none of the tested mice died at the dosage of 1.638 g/kg, which is the maximum tolerated dosage for mice.

50 ICR derived mice, half male and half female, weighing 18-22 grams, provided by animal labs of Anti-Bacterial Industrial Research Institute of Szuchuan province, China were used as test animals. The test solution was prepared by using 0.5% CMC to disintegrate the capsule, containing geranium oil and extraction from *Sophora* roots, and suspension solutions added to obtain the required concentration. The 50 mice were then divided into 5 groups, with 10 mice in each group (half are male and half are female). The 5 groups of mice were given the composition orally at various dosages of 4.000 g/kg, 3.200 g/kg, 2.560 g/kg, 2.048 g/kg, and 1.638 g/kg respectively. The dosages between the groups have a proportional value of 1:0.8. The drug was administered once to all the mice, and the mice were subsequently observed for 14 days for any death. On the third day after the drug administration, some mice start dying, and before death there were twitching, shortness of breath, and stop of food intake. FIG. 2 shows the results of the experiment. The LD$_{50}$ dosage is 2.35 g/kg with a range of 2.10 to 2.62 g/kg (P=0.95).

Figure 3:
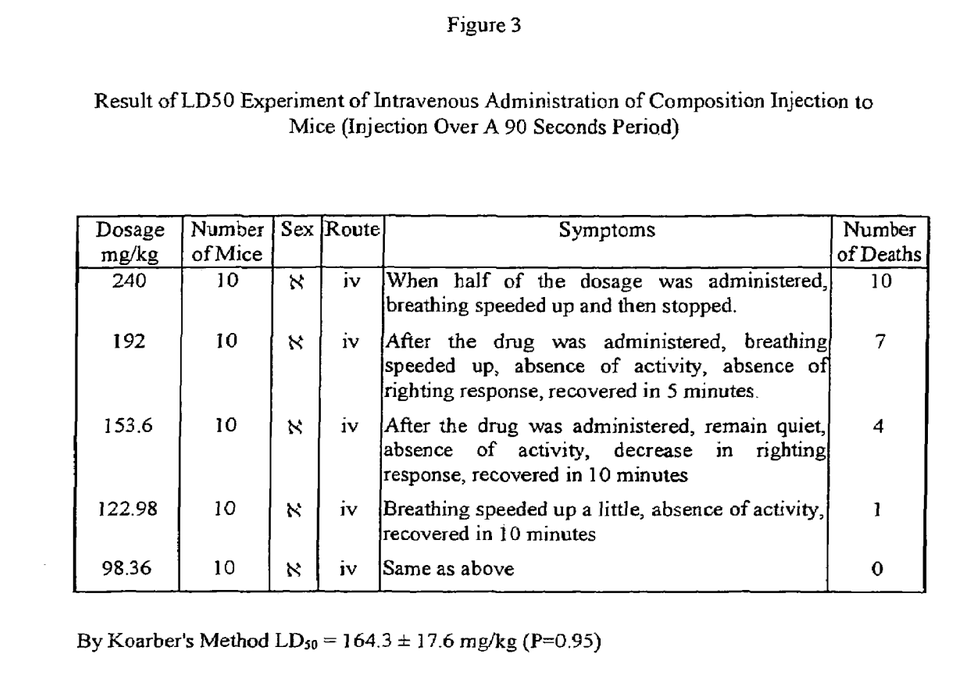
FIG. 3 shows the result of a $LD_{50}$ experiment involving intravenous administration of a composition of the present invention in injection form to mice. According to the result, half of the tested mice will die at the dosage of 164.3±17.6 mg/kg of composition injection, and none of the tested mice died at the dosage of 98.36 mg/kg, which is the maximum tolerated dosage for mice.

LD$_{50}$ Animal Experiment With Intravenous Administration 50 healthy female mice, weighing 18-22 grams, from Kunming City of Yunan Province, China were used as test animals. The 50 mice were then divided into 5 groups, with 10 mice in each group. A 2 ml composition injection containing 198.30 mg-198.76 mg of geranium oil and 1.24 mg-1.70 mg of total alkaloids of *Sophora* roots were administered intravenously to all the mice through their veins at the tails at a speed of 90 seconds/shot. The shots were administered to all the mice once and the mice were subsequently observed for 7 days for the number of deaths. FIG. 3 shows the results of the experiment. The LD$_{50}$ dosage is 164.3 mg/kg±17.6 mg/kg (P=0.95).

Figure 4:
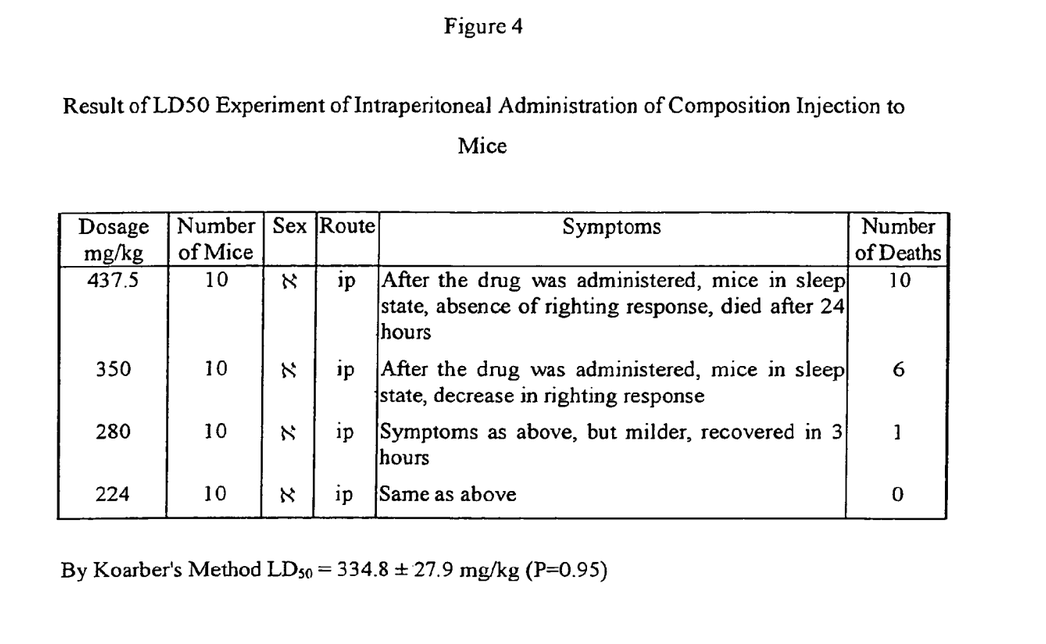
FIG. 4 shows the result of a $LD_{50}$ experiment involving intraperitoneal administration of a composition of the present invention in injection form to mice. According to the result, half of the tested mice will die at the dosage of 334.8±27.9 mg/kg of composition injection, and none of the tested mice died at the dosage of 224 mg/kg, which is the maximum tolerated dosage for mice.

LD$_{50}$ Animal Experiment With Intraperitoneal Administration 50 healthy female mice, weighing 18-22 grams, provided by Kunming City of Yunan Province, China were used as test animals. The 50 mice were then divided into 5 groups, with 10 mice in each group. A 2 ml injection containing 198.30 mg-198.76 mg of geranium oil and 1.24 mg-1.70 mg of total alkaloids of the *Sophora* roots were administered intraperitoneally to all the mice. The shots were administered to all the mice once and the mice were subsequently observed for 7 days for the number of deaths. FIG. 4 shows the results of the experiment. The LD$_{50}$ dosage is 334.3 mg/kg±27.9 mg/kg (P=0.95).

The composition can be used as a supporting drug or an adjunct supplement to chemotherapy and radiation therapy treatments to reduce the side effect of bone marrow suppression of such treatments. The composition can be administered prior to and or after the treatment. The dosages to be used for animals and humans are derived as shown in FIG.5, FIG. 6, and FIG.7 for oral, intravenous, and intraperitoneal administrations respectively.

From FIG. 5, one can see that the feasible dosages for oral administration of the composition to animals treated with chemotherapy and or radiation therapy should preferably be between 1,638 mg/kg/day and 150 mg/kg/day. Oral administration of the composition capsule to Humans treated with chemotherapy and or radiation therapy would preferably be between 24.57 capsules/60 kg/day to 2.25 capsules/60 kg/day. Oral administration of the extractions of the two herbs of the composition to humans would preferably be 9,778.86 mg/60 kg/day to 877.50 mg/60 kg/day of geranium oil and 245.70 mg/60 kg/day to 4.50 mg/60 kg/day of extractions from *Sophora* roots. Oral administration of the actual herbs to humans would preferably be 9,778,860 mg/60 kg/day to 877,500 mg/60 kg/day of *Pelargonium graveolens* and 8,190 mg/60 kg/day to 150 mg/60 kg/day of *Sophora* roots.

From FIG. 6, one can see that the feasible dosages for intravenous administration of the composition to animals treated with chemotherapy and or radiation therapy would preferably be 98 mg/kg/day to 25 mg/kg/day. Intravenous administration of the composition to humans treated with chemotherapy and or radiation therapy would preferably be between 2.94 ampoule/60 kg/day to 0.75 ampoule/60 kg/day. Intravenous administration of the extractions of the two herbs of the composition to humans would preferably be 584.35 mg/60 kg/day to 148.73 mg/60 kg/day of geranium oil and 5.00 mg/60 kg/day to 0.93 mg/60 kg/day of *Sophora* roots extracts.

From FIG. 7, one can see that the feasible dosages for intraperitoneal administration of the composition to animals treated with chemotherapy and or radiation therapy would preferably be 224 mg/kg/day to 25 mg/kg/day. Intraperitoneal administration of the composition to humans treated with chemotherapy and/or radiation therapy would preferably be 6.72 ampoule/60 kg/day to 0.75 ampoule/60 kg/day.

Intraperitoneal administration of the extractions of the two herbs of the composition to humans would preferably be 1335.67 mg/kg/day to 148.73 mg/kg/day of geranium oil and 11.42 mg/kg/day to 0.93 mg/kg/day of *Sophora* roots extracts.

EXAMPLE

Shots are administered to mice, with regular immune systems, that are also given the 5-Fu drug orally.

The test substance is prepared by dissolving the content of the 2 ml injection in 0.025% Tween 80 in 5% Dextrose.

Animals tested are 24 male ICR derived mice weighing 22±2 grams provided by animal breeding center of MDS Pharma Services—Taiwan, Ltd.(Formerly Panlabs). The animals are divided into three groups of 8 mice. All aspects of the work including housing, experimentation and disposal of animals were performed in general according to the International Guiding Principles for Biomedical Research Involving Animals (CIOMS Publication No. ISBN 92 90360194, 1985).

A dosage of 100 mg/kg of test substance and 50 mg/kg of test substance and a vehicle control, 0.025% Tween 80 in 5% Dextrose, were administered to three groups of test animals respectively. The test substance and control were administered intraperitoneally to the test animals 24 hours before and 1 hour after a single dose of the chemotherapeutic agent 5-fluorouracil (5-Fu) (100 mg/kg, PO) and then once daily for the next 5 consecutive days (7 does in total). On day 8, the test animals were bled retroorbitally to determine the cell counts of erythrocytes (RBC), platelets (PLT), and total leukocytes (WBC) and differential leukocytes counts: granulocytes (GR), monocytes (MO), and lymphocytes (LY). The mean±SEM of cell counts was calculated for each group of treatments and unpaired Student's t test was applied for comparisons between vehicle and test substance treated groups. Differences were considered significant at P<0.05. FIG. 8 and FIG. 9 show the results of the experiment.

The total blood cells counts (erythrocytes, platelets, leukocytes) of the group of animals treated with 5-Fu and 7 doses of 50 mg/kg of the composition injection increased across the board as compared to test animals treated with 5-Fu only. See FIG. 8.

The total leukocyte count of the group of animal treated with 5-Fu and 7 doses of 50 mg/kg of the composition injection increased significantly as compared to test animals treated with 5-Fu only. In particular, the differential leukocyte count shows that both the granulocytes and lymphocytes counts increased significantly. A normal mouse's leukocyte cell count is 8.05±0.58 $10^3$/ul, and the control test animals treated with 5-Fu have an average leukocyte count of 2.86±0.37 $10^3$/ul. On the other hand, test animals treated with the 50 mg/kg test substance and 5-Fu have an average leukocyte count of 4.60±0.24 $10^3$/ul, showing only 33.50% of the bone marrow suppression effect of 5-Fu when compared with the control. A normal mouse's granulocyte count is 1.90+0.37 $10^3$/ul, and its lymphocyte count is 3.94±0.55 $10^3$/ul. Differential leukocyte count shows that the suppression effect with respect to granulocytes in test animals treated with 50 mg/kg test substance and the 5-Fu is only 42.70% of that of the control. With respect to lymphocytes, the suppression effect is in test animals treated with 50 mg/kg test substance and the 5-Fu is only 51.20% of that of the control. The result of the experiment shows that the composition, when used with 5-Fu, significantly reduced the bone marrow suppression effect with respect to erythrocytes, platelets, and leukocytes, and in particular with respect to granulocytes and lymphocytes. The ability of the composition of geranium oil and extracts from *Sophora* roots to reduce the bone marrow suppression effect makes it a good candidate as a supporting drug or supplement to be used in cancer treatments that induce such bone marrow suppression side effect. In particular, the composition may be used with chemotherapy and or radiation therapy to increase the leukocyte count. For example, the composition may be used with 5-Fu, doxorubincin and other chemotherapeutic agents just as Neupogen is also used with 5-Fu as well as doxorubincin and many other type of chemotherapy to stimulate the growth of neutrophils.

Modifications and variations of the invention as hereinbefore set forth can be made without departing from the spirit and scope thereof, and therefore, only such limitations should be imposed as are indicated by the appended claims.

What is claimed is:

1. A method for reducing bone marrow suppression side effect of one or more cancer treatments, the method comprising:
   (a) identifying one or more mammalian animals being treated or in need of treatment with one or more cancer treatments, wherein a cancer treatment comprises delivering one or more doses of a therapy at one or more time intervals; and
   (b) administering to the one or more mammalian animals a therapeutically effective dosage of a composition comprising geranium oil and extractions from roots of one or more plants from the genus *Sophora* and/or from *Euchresta strigillosa*, wherein the therapeutically effective dosage is administered before and after delivery of at least one of the one or more doses of therapy, thereby increasing platelet and leukocyte counts in said one or more mammalian animals.

2. The method of claim 1, wherein said one or more mammalian animals are one or more humans.

3. The method of claim 1, wherein said one or more mammalian animals are one or more canines.

4. The method of claim 1, wherein said one or more mammalian animals are one or more monkeys.

5. The method of claim 1, wherein said one or more mammalian animals are non-rodents.

6. The method of claim 1, wherein said one or more mammalian animals are rodents.

7. The method of claim 6, wherein said rodents are mice.

8. The method of claim 6 wherein said rodents are rats.

9. The method of claim 6, wherein said rodents are rabbits.

10. The method of claim 6, wherein said rodents are hamsters.

11. The method of claim 1, wherein said one or more cancer treatments induce a leukopenia side effect.

12. The method of claim 1, wherein said one or more cancer treatments comprise administering one or more chemotherapeutic agents.

13. The method of claim 12, wherein said chemotherapeutic agent induces the bone marrow suppression side effect.

14. The method of claim 12, wherein said chemotherapeutic agent induces a the leukopenia side effect.

15. The method of claim 12, wherein said chemotherapeutic agent is 5-Fluorouracil.

16. The method of claim 12, wherein said chemotherapeutic agent is doxorubincin.

17. The method of claim 1, wherein said one or more cancer treatments comprise administering radiation therapy.

18. The method of claim 1, wherein said geranium oil is extracted from one or more species of the genus *Pelargonium*.

19. The method of claim 18, wherein said geranium oil is extracted from the species *graveolens*.

20. The method of claim 18, wherein said geranium oil is extracted from the species *roseum*.

21. The method of claim 18, wherein said geranium oil is extracted from the species *terebinthinaceum*.

22. The method of claim 1, wherein said composition comprises ef citronellol, geraniol, geranyl formate, citronellyl formate, matrine, and oxymatrine.

23. The method of claim 1, wherein said extractions are from roots *Sophora*.

24. The method of claim 1, wherein said composition comprises citronellol, geraniol, geranyl formate, citronellyl formate, linalool, Trans-Rose Oxide, Cis-Rose Oxide, kurarinol, matrine, oxymatrine, and sophocarpine.

25. The method of claim 1, wherein said composition comprises geranium oil, matrine and oxymatrine.

26. The method of claim 1, wherein said composition comprises citronellol, geraniol, citronellyl formate, geranyl formate and extractions from roots of at least one plant selected from *Sophora flavescenes, Sophora tonkinensis, Sophora subprostrata, Sophora alopecuroides, Sophora moorcroftiana,* and *Euchresta strigillosa*.

27. The method of claim 1, wherein said composition comprises A and B wherein A is selected from hexanol, 3-hexen-1-ol, α-pinene, β-pinene, P-cymene, limonene, 1,8-cineol, ocimene, linallol oxide, linallol, trans-rose oxide, cis-rose oxide, citronellal, menthone, iso-menthone, menthol, terpineol, citronellol, geraniol, citronellyl formate, geranyl formate, caryophellene, citronellyl propionate, gurjunene, and cadiene, and B is selected from matrine, oxymatrine, sophoranol, N-methylcytisine, anagyrine, baptifoline, sophocarpine, sophoridine, isomatrine, 7, 11-dehydromatrine, sophoramine, 7-dehydrosophoramine, 9hydroxysophoramine, 5α,9α-dihydroxymatrine, N-oxysophocarpine; sophoranol N-oxide, rhombifoline, lupanine, mamanine, kuraramine, isokuraramine, and kurarinol.

28. The method of claim 1, wherein said composition further comprises a pharmaceutically acceptable solvent.

29. The method of claim 28, wherein said pharmaceutically acceptable solvent comprises a mixture of about 0.025% polyoxyethylenesorbitan monooleate in about 5% Dextrose.

30. The method of claim 28, wherein said pharmaceutically acceptable solvent comprises a mixture of about 0.026% to about 20% polyoxyethylenesorbitan monooleate in about 5% Dextrose.

31. The method of claim 1, wherein said composition further comprises a pharmaceutically acceptable carrier.

32. The method of claim 31, wherein said pharmaceutically acceptable carrier is water.

33. The method of claim 1, wherein the administering comprises orally administering a theraputically effective dosage of said composition to the one or more mammalian animals.

34. The method of claim 33 wherein said dosage is in a range of between about 9,828 mg/60 kg/day and about 900 mg/60 kg/day.

35. The method of claim 33, wherein the orally administering comprises administering an oil capsule comprising said composition to the one or more mammalian animals.

36. The method of claim 33, wherein the orally administering comprises administering a tablet comprising said composition to the one or more mammalian animals.

37. The method of claim 33, wherein the orally administering comprises administering a pill comprising said composition to the one or more mammalian animals.

38. The method of claim 33, wherein the orally administering comprises administering pastes comprising said composition to the one or more mammalian animals.

39. The method of claim 33, wherein the orally administering comprises administering food additives comprising said composition to the one or more mammalian animals.

40. The method of claim 33, wherein the orally administering comprises administering a dietary supplement comprising said composition to the one or more mammalian animals.

41. The method of claim 33, wherein the orally administering comprises administering health food comprising said composition to the one or more mammalian animals.

42. The method of claim 33, wherein the orally administering comprises administering a liquid comprising said composition to the one or more mammalian animals.

43. The method of claim 33, wherein the orally administering comprises administering a syrup comprising said composition to the one or more mammalian animals.

44. The method of claim 33, wherein the orally administering comprises administering decoction soup comprising said composition to the one or more mammalian animals.

45. The method of claim 33, wherein the orally administering comprises administering edible geranium oil and extractions of roots of at least one plant selected from *Sophora flavescens, Sophora tonkinensis, Sophora subprostrata, Sophora alopecuroides, Sophora moorcroftiana*, and *Euchresta strigillosa*.

46. The method of claim 33, wherein the orally administering comprises administering geranium oil and powder of roots of at least one plant selected from *Sophora flavescens, Sophora tonkinensis, Sophora subprostrata, Sophora alopecuroides, Sophora moorcroftiana*, and *Euchresta strigillosa*.

47. The method of claim 33, wherein the orally administering comprises administering geranium oil and pastes made from roots of at least one plant selected from *Sophora flavescens, Sophora tonkinensis, Sophora subprostrata, Sophora alopecuroides, Sophora moorcroftiana*, and *Euchresta strigillosa*.

48. The method of claim 33, wherein the orally administering comprises administering geranium oil and soup mixture from decocting roots of at least one plant selected from *Sophora flavescens, Sophora tonkinensis, Sophora subprostrata, Sophora alopecuroides, Sophora moorcroftiana*, and *Euchresta strigillosa*.

49. The method of claim 33, wherein the orally administering comprises administering extractions from roots of at least one plant selected from *Sophora flavescens, Sophora tonkinensis, Sophora subprostrata, Sophora alopecuroides, Sophora moorcroftiana*, and *Euchresta strigillosa* and soup mixture from decocting *Pelargonium* plant.

50. The method of any of claims 33, 35, 44, 45, 46, 47, 48, or 49 wherein said composition has a ratio with geranium oil in the range of between about 97.5% and about 99.5% and extractions from roots of *Sophora flavescens* in the range of between about 2.5% and about 0.5%.

51. The method of claim 1, wherein the administering comprises administering intraperitoneally a therapeutically effective dosage of said composition to the one or more mammalian animals.

52. The method of claim 51, wherein said dosage is in a range of between about 1,344 mg/60 kg/day and about 150 mg/60 kg/day.

53. The method of claim 1, wherein the administering comprises administering intravenously a therapeutically effective dosaae of said composition to the one or more mammalian animals.

54. The method of claim 53, wherein said dosage is in a range of between about 588 mg/60 kg/day and about 150 mg/60 kg/day.

55. The method of claim 51 or 53, wherein said composition has a ratio with geranium oil in the range of between about 99.15% and about 99.38% and extractions from roots of *Sophora flavescens* in the range of between about 0.62% and about 0.85%.

56. A method for reducing bone marrow suppression side effect of one or more cancer treatments, the method comprising:
(a) identifying one or more mammalian animals being treated or in need of treatment with one or more cancer treatments, wherein a cancer treatment comprises delivering one or more doses of a therapy at one or more time intervals; and
(b) administering to the one or more mammalian animals a therapeutically effective dosage of geranium oil and separately administering a therapeutically effective dosage of extractions from roots of one or more Glants from the genus *Sophora* and/or from *Euchresta strigillosa*, wherein the dosage of geranium oil and the dosage of extractions from one or more plants from *Sophora* and/or *Euchresta strigillosa* are delivered separately at an interval of one to fourteen days thereby increasing platelet and leukocyte counts in said one or more mammalian animals.

57. The method of claim 56, wherein said interval is within forty-eight hours.

58. The method of claim 56, wherein said interval is within twenty-four hours.

59. The method of claim 56, wherein said extractions are from roots of at least one plant selected from *Sophora flavescenes, Sophora tonkinensis, Sophora subprostrata, Sophora alopecuroides, Sophora moorcroftiana*, and *Euchresta strigillosa*.

* * * * *

UNITED STATES PATENT AND TRADEMARK OFFICE
CERTIFICATE OF CORRECTION

PATENT NO.        : 7,387,806 B2                                    Page 1 of 1
APPLICATION NO.   : 10/984246
DATED             : June 17, 2008
INVENTOR(S)       : Andy A. T. Fong and Guang-Tzuu Shane It is certified that error appears in the above-identified patent and that said Letters Patent is hereby corrected as shown below:

Title page,

"Assignee: Medigreen Biotechnology Inc., Panchiao Taipei (TW" should read

--Assignee: Medigreen Biotechnology Corp., Banciao City, Taipei (TW--.

Claim 14, col. 10, line 11,

"induces a the leukopenia side effect" should read

--induces the leukopenia side effect--.

Claim 22, col. 10, lines 26-27,

"comprises ef citronellol" should read --comprises citronellol--.

Claim 26, col. 10, line 40,

"Sophora flavescenes" should read --Sophora flavescens--.

Claim 33, col. 11, line 4,

"theraputically" should read --therapeutically--.

Claim 50, col. 12, lines 10-11,

"claims 33, 35, 44, 45, 46, 47, 48, or 49" should read

--claims 33, 35, 36, 37, 38, 39, 40, 41, 42, 43, 44, 45, 46, 47, 48, or 49--.

Claim 53, col. 12, line 24,

"dosaae" should read --dosage--.

Claim 56, col. 12, line 45,

"GIants" should read --plants--.

Claim 59, col. 12, lines 58-59,

"Sophora flavescenes" should read --Sophora flavescens--.

Signed and Sealed this

Thirteenth Day of April, 2010

David J. Kappos
*Director of the United States Patent and Trademark Office*